United States Patent [19]

Vahlne et al.

[11] Patent Number: 5,283,320
[45] Date of Patent: Feb. 1, 1994

[54] PEPTIDES FOR HTLV-2 INFECTION DIAGNOSIS OF, THERAPY FOR, VACCINATION AGAINST, FOR DISTINGUISHING BETWEEN HTLV-1 AND HTLV-2 INFECTIONS AND ANTIBODIES DERIVED THEREFROM

[75] Inventors: Anders Vahlne, Hovas; Bo Svennerholm, Gothenburg; Lars Rymo, Hovas; Stig Jeansson; Peter Horal, both of Gothenburg, all of Sweden

[73] Assignee: Syntello AB, Gothenburg, Sweden

[21] Appl. No.: 434,239

[22] Filed: Nov. 13, 1989

[51] Int. Cl.$^5$ .................. C07K 7/10; A61K 37/02
[52] U.S. Cl. ............................................. 530/325
[58] Field of Search ..................... 530/325; 514/12

[56] References Cited

FOREIGN PATENT DOCUMENTS 8908664  9/1989  World Int. Prop. O. .

OTHER PUBLICATIONS

Seiki, et al, Proc. Natl. Acad. Sci., vol. 80, pp. 3618–3622, 1983.
Perkins, et al, Science, pp. 421–424, 1984.
Barany et al., "Solid Phase Peptide Synthesis", in: The Peptides, vol. 2, Academic Press, Inc. pp. 1–284 (1979).
Cabradilla et al., "Serodiagnosis of Antibodies to the Human AIDS Retrovirus With a Bacterially Synthesized env Polypeptide", Bio/technology, 4:128–133 (1986).
Chang et al., "Detection of Antibodies to Human T-cell Lymphotropic Virus-III (HTLV-III) With an Immunoassay Employing a Recombinant *Escherichia coli*-Derived Viral Antigenic Peptide", Bio/technology, 3:905–909 (1985).
Erickson et al., "Solid Phase Peptide Synthesis", in: The Proteins, 3rd Edition, vol. 2, Academic Press Inc., Chapter 3 pp. 255–527 (1976).
Gallo et al., "Comparison of Immunofluorescence, Enzyme Immunoassay, and Western Blot (Immunoblot) Methods for Detection of Antibody to Human T-Cell Leukemia Virus Type 1", J. Clin. Micro., 26:1487–1491 (1988).

Gurtler et al., "Sensitivity and Specificity of Commercial ELISA Kits for Screening Anti-LAV/HTLV III", J. Virol. Met., 15:11–23 (1987).
Kieny et al., "AIDS VIRUS env Protein Expressed From a Recombinant Vaccinia Virus", Bio/technology, 4:790–795 (1986).
Lee et al., "High Rate of HTLV-II Infection in Seropositive IV Drug Abusers in New Orleans", Science, 244:471–475 (1989).
Lerner, "Antibodies of Predetermined Specificity in Biology and Medicine", Advances in Immunol., 36:1–44 (1984).
Lerner et al., "The Development of Synthetic Vaccines", in: The Biology of Immunologic Disease, Dixon and Fisher eds. Sinaur Associates Inc. MA, pp. 331–338 (1983).
Marx, "Leukemia Virus Linked to Nerve Disease", Science, 236: 1059–1061 (1987).
Putney et al., "HTLV-III/LAV-Neutralizing Antibodies to an *E. coli*-Produced Fragment of the Virus Envelope", Science, 234: 1392–1395 (1986).
Robert-Guroff et al., "Prevalence of Antibodies to HTLV-1, -II and -III in Intravenous Drug Abusers From an AIDS Endemic Region", J.A.M.A., 255:3133–3137 (1986).

(List continued on next page.)

Primary Examiner—Lester L. Lee
Assistant Examiner—S. G. Marshall
Attorney, Agent, or Firm—Knobbe, Martens, Olson & Bear

[57] ABSTRACT

Peptides corresponding to epitopes of HTLV-2 proteins are provided. These peptides are immunologically reactive with HTLV-2 specific antibodies. Several of the peptides are sufficiently unreactive to antibodies to HTLV-1 to distinguish between antibodies which recognize HTLV-1 and those which recognize HTLV-2. Thus HTLV-1 infections can be distinguished from HTLV-2 infections. The peptides are useful in assays for detection of HTLV-2 infection or exposure. The peptides are also useful as vaccine compositions against HTLV-2. Antibodies generated in response to immunization by the peptides are also provided.

2 Claims, No Drawings

OTHER PUBLICATIONS

Type II: An open Readinjg Frame for the Protease Gene", Proc. Natl. Acad. Sci. USA, 82:3101-3105 (1985).
Tedder et al., "Low Prevalance in the UK of HTLV-I and HTLV-II Infection in Subjects with AIDS, With Extended Lymphadenopathy, and at Risk of AIDS", Lancet, Jul. 21, 1984 p. 125-127.
Vernant et al., "Endemic Tropical Spastic Paraparesis Associated With Human T-Lymphotropic Virus Type I: A Clinical and Seroepidemiological Study of 25 Cases", Ann. Neurol., 21:123-130 (1987).
Rodgers-Johnson et al., "HTLV-I and HTLV-III Antibodies and Tropical Spastic Paraperesis", Lancet, Nov. 30, 1985 pp. 1247-1248.
Rosenblatt et al., "Integrated Human T-Cell Leukemia Virus II Genome in CD8+ T Cells From a Patient With Atypical Hairy Cell Leukemia: Evidence for Distinct T and B Cell Lymphoproliferative Disorders", Blood, 71:363-369 (1988).
Rosenblatt et al., "A Second Isolate of HTLV-II Associated with Atypical Hairy-Cell Leukemia", New Engl. J. Med., 315:372-377 (1986).
Sarngadharan et al., "Human T-cell Leukemia Viruses", Virology, Chapter 58:1345-1371 (1985).
Shaw et al., "Human T-Cell Leukemia Virus: Its Discovery and Role in Leukemogenesis and Immunosuppression", Year Book Medical Publishers, Inc., pp. 1-27 (1984).
Shimotohno et al., "Complete Nucelotide Sequence of an Infections Clone of Human T-Cell Leukemia Virus

PEPTIDES FOR HTLV-2 INFECTION DIAGNOSIS OF, THERAPY FOR, VACCINATION AGAINST, FOR DISTINGUISHING BETWEEN HTLV-1 AND HTLV-2 INFECTIONS AND ANTIBODIES DERIVED THEREFROM

BACKGROUND OF THE INVENTION

The present invention relates to synthetic peptides the sequences of which correspond to regions of immunologically important proteins of Human T-cell Lymphotropic Virus Type II (HTLV-2). These peptides are useful as diagnostic reagents for detecting the presence of antibodies to HTLV-2. The peptides may also be useful as immunogens in a vaccine composition to elicit antibodies against and prevent infection by HTLV-2.

HTLV-2 and Human T cell Lymphotropic Virus Type I (HTLV-1) are genetically and antigenically related members of a family of oncogenic retroviruses sharing a tropism for T lymphocytes and an association with lymphoproliferative diseases. Due to the degree of homology between HTLV-1 and HTLV-2, serological studies have been unable to differentiate between infection by HTLV-1 and HTLV-2. Unequivocal differentiation of HTLV-1 and HTLV-2 requires virus isolation and/or molecular identification.

HTLV-1 is endemic to southern Japan, and parts of the Caribbean, South America, Southeast United States and Central Africa. HTLV-1 is the etiologic agent of adult T-cell leukemia/lymphoma (ATL). Sarngadharan et al., Virology, (B.N. Fields et al., eds) pp. 1345-137,1 (1985). HTLV-1 is most prevalent in parts of Japan where approximately up to 15% of the population has been infected. Recently, HTLV-1 has been linked to the disease tropical spastic paraperesis (TSP) also known as HTLV-1 associated myelopathy (HAM) in Japan. Rodgers-Johnson et al., Lancet, 2:1247 (1985); Vernant et al., Ann. Neurol., 21:123 (1987). In the tropics, TSP is of the same magnitude and importance as the multiple sclerosis syndrome is in the western world. Marx, Science 236:1059–1061 (1987).

HTLV-2, in contrast, has not been definitely associated with human disease nor has it been shown to be endemic to any known population. The HTLV-2 virus has been isolated from two patients with T cell variants of hairy cell leukemia. Rosenblatt et al., New Engl. J. Med., 315:372–377 (1986). One of these HTLV-2 positive patients also had a co-existing CD8+ lymphoproliferative disorder. Rosenblatt et al., Blood, 71:363–369 (1988).

Significantly, intravenous drug abusers (IVDAs) previously thought to be infected with HTLV-1 have now been found to be infected by HTLV-2. It is now thought that HTLV-2 infection may be quite common among IVDAs. Tedder et al., Lancet, 2:15–128, (1984); and Robert-Guroff et al., J. Amer. Med. Assn., 255:3133–3137 (1986). This was recently supported by a study using PCR amplification which detected HTLV-2 related nucleotide sequences in a group of IVDAs from New Orleans. Lee et al., Science, 244:471–474 (1989). From serological studies reported from parts of the United States it has been shown that IVDAs may be infected with HTLV-1 and/or HTLV-2 with seropositivity rates as high as 24%. Gallo et al., J. Clin. Micro., 26:1487–1491 (1988).

Currently available tests for detection of viral infections rely on the detection of antibodies to the virus or portions thereof. Methods being developed for detecting HTLV infection, in general, will measure exposure to the virus by detecting and quantifying antibodies to HTLV antigens in blood, sera, and blood-derived products. Assays commonly used in diagnosis of other viral infections would be of immeasurable use in screening blood and blood products for previous exposure to HTLV-1 and/or HTLV-2. Due to the relatedness of the two viruses, it has been impossible to distinguish between infection by HTLV-1 or HTLV-2 using currently available immunological methods. Consequently, the virus is isolated from the patient and then distinguished on the basis of its nucleotide sequence. Often the virus must be propagated in vitro to provide enough material to test. Virus isolation is particularly difficult and dangerous in the case of IVDAs since they are often infected with human immunodeficiency virus (HIV) the causative agent of acquired immunodeficiency syndrome (AIDS).

Recently, the study of viral DNA has been aided by the use of polymerase chain reaction (PCR). However, PCR may still require virus isolation to obtain sufficient material.

An automated blood screening test format capable of readily detecting HTLV-2 infection and distinguishing HTLV-1 infection from HTLV-2 infection is critical to a supply of uninfected blood. Current methods of HTLV-1 screening cannot discern between HTLV-1 and HTLV-2 quickly and inexpensively.

The source of antigens for assays to detect HTLV-1 infection has until now included HTLV-1 proteins obtained from HTLV-1 infected T cell lines and antigens produced by recombinant DNA techniques. In theory, antigens for use in detecting HTLV-2 infection would be obtained from the same sources. The use of antigens obtained from these sources, however, has significant drawbacks in addition to their crossreactivity with HTLV-2.

The production of HTLV-2 per se in continuous cell lines must be performed in high risk (P3 containment) laboratories due to the danger to investigators who may become adversely exposed to the virus. In addition, protein antigens have been shown to give false negative and false positive results. For instance, enzyme linked immunosorbent assay (ELISA) tests utilizing whole virus HIV-1 antigens obtained from cell lines are prone to such errors. Gurtler et al., J. Virological Methods, 15:11–23 (1987). It is likely that similarly unreliable results will be obtained with cell-derived HTLV-2 antigens. Western blot analyses, for HTLV-2 detection using electroblotted whole virus antigens, may provide greater specificity but this method is laborious, time-consuming and not easily automated. Furthermore, since cells producing HTLV-2 are of human origin, viral antigens obtained from these cell lines, unless exhaustively purified, are likely to be contaminated with normal cellular antigens, such as HLA antigens, which could produce false positive reactions in an ELISA test.

Exhaustive purification of viral antigens from cell lines can also destroy immunogenicity of immunologically important proteins or otherwise inactivate antigens, thereby producing reagents that result in false negative reactions. In addition, false negative reactions using live virus derived antigens may occur because of steric hindrance whereby antibodies cannot react with their specific antigens because the reaction is blocked by the presence of other antigens and antibodies in the reaction mixture.

Proteins isolated from live virus can be unsuitable for vaccination due to the risk of contamination by whole virus or virus genomes.

ELISA tests to detect HTLV-2 infection may also employ immunologically important viral proteins produced by cloning portions of the HTLV-2 genome in various expression systems such as bacteria, yeast or vaccinia. The complete nucleotide sequence of HTLV-2 has been reported and the viral envelope glycoproteins and core proteins respectively encoded by the env and gag genes of HTLV-2, are apparently antigens recognized by antibodies in the sera of patients with HTLV-2 and HTLV-1 infections. Shimitohno et al., Proc. Natl. Acad. Sci. USA, 82:3101-3105 (1985).

Recombinant antigens purified from the host, may be used in diagnosis and as potential vaccine compositions as has been done for HIV-1 proteins. Cabradilla et al., Biotechnology, 4:128-133 (1986); Chang et al., Biotechnology, 3:905-909 (1985); Putney et al., Science, 234:1392-1395 (1986); and Kieny et al., Biotechnology, 4:790-795 (1986). As diagnostics, HTLV-2 antigens produced by recombinant DNA methods, however, will still have to be exhaustively purified to avoid false positive reactions in the ELISA due to any antibody reactivity to host antigens which are likely to contaminate the HTLV-2 antigen preparation unless exhaustively purified. Also, denaturation of HTLV-2 antigens during purification may destroy important antigenic regions.

In the case of vaccines, recombinant proteins purified from bacteria or yeast are often contaminated with bacterial or yeast proteins. Even minute amounts of these contaminants are capable of causing adverse reactions in patients.

Materials which approach 100% accuracy and specificity in diagnosis of HTLV-2 would be valuable given the nature of the diseases caused by HTLV-1 and possible diseases caused by HTLV-2 and the need for accurate type specific results.

SUMMARY OF THE INVENTION

In accordance with the present invention, four novel peptides corresponding to epitopes of HTLV-2 proteins are provided. These peptides can be utilized alone or in combination, uncoupled or coupled to other molecules. The peptides are useful in selective diagnostic methods for detecting HTLV-2 infections, in immunization against HTLV-2 infection and in production of polyclonal and monoclonal antibodies.

DESCRIPTION OF THE INVENTION

The present invention provides four peptides which have been synthesized and tested for immunoreactivity to HTLV-2 positive serum samples. The peptides correspond to regions of the envelope glycoprotein (env), and one core protein of HTLV-2. The novel peptides can be used alone or in combination, in solution or coupled to solid supports. The peptides can be used for tests to diagnose HTLV-2 infection and to distinguish between HTLV-1 and HTLV-2 infections. The peptides can also be used as immunogens in vaccine compositions and to elicit polyclonal or monoclonal antibody production to HTLV-2.

Proteins contain a number of antigenic determinants or epitopes which are the regions of the proteins comprising the recognition and binding sites for specific antibodies. In general, proteins contain between 5 to 10 epitopes, each of which contains a sequence of 6 to 8 amino acids. Epitopes can be either continuous, in which the 6 to 8 amino acids are present in linear sequence, or discontinuous, in which the amino acids that form the epitope are brought together by the three dimensional folding of the protein. Even though an epitope constitutes only a relatively few amino acids, its reactivity with an antibody may be influenced by the amino acids in the protein which surround the epitope.

Studies aimed at mapping antigenic sites or epitopes of proteins have been aided by the use of synthetic peptides corresponding to various regions of the proteins of interest. Lerner et al., in, The Biology of Immunological Disease: A Hospital Practice Book, (Dixon and Fisher, eds.) pp. 331-338 (1983); and Lerner, Adv. Immunol., 36:1 (1984). In addition to their usefulness in epitope mapping studies, synthetic peptides, if encompassing major antigenic determinants of a protein, have potential as vaccines and diagnostic reagents. Synthetic peptides have several advantages with regard to specific antibody production and reactivity.

The exact sequence of the synthesized peptide can be selected from the amino acid sequence of the protein as determined by amino acid sequencing of the protein or predicted from the DNA sequence coding for the protein. The use of specific synthetic peptides eliminates the need for using the full-length protein in the production of or assay for antibodies. Furthermore, the solid phase peptide synthetic techniques of Merrifield and coworkers allow for essentially unlimited quantities of the synthesized peptide of interest to be chemically produced. Erickson and Merrifield in The Proteins, 3rd Edit., Vol. 2, Academic Press, New York, Chapter 3 (1976). The availability of automated peptide synthesizers has further advanced such techniques.

Although a variety of criteria can be used to determine which regions of proteins are immunodominant, peptides corresponding to such regions may not always be useful in large-scale screening and diagnosis. For example, antigenicity may be lost because the peptide is not in the proper spatial orientation to be recognized by antibodies which react with the protein. Furthermore, as is particularly evident with HIV-1 and HIV-2, there is significant genetic variability within each of these two virus groups leading to many serotypes, or isolates, of the viruses. This has put a significant constraint on choosing a region of a protein from which to derive a peptide for use in screening and diagnosis and in formulating immunogens. However, certain immunodominant portions of HIV-1 and HIV-2 proteins have been found to be relatively invariant.

Recently, such immunologically reactive peptides corresponding to various immunodominant regions of the surface glycoproteins gp120 and gp41 from HIV-1 and the corresponding proteins of HIV-2 encoded by the env gene of the two viruses have been synthesized and shown to react with about 100% efficiency with sera from HIV-1 or HIV-2 infected individuals. When used in assays for detecting the presence of antibodies, such peptides gave apparently no false positive or false negative reactions.

Synthetic peptides corresponding to regions of immunologically important proteins of HTLV-2 have now found immediate use in diagnostic methods for detection of HTLV-2, differentiation between HTLV-1 and HTLV-2 infection, as potential vaccines for HTLV-2 and for the production of polyclonal and monoclonal antibodies.

The peptides encompassed by the invention comprise amino acid sequences each containing at least one continuous (linear) epitope reactive with HTLV-2 specific antibodies.

The invention thus encompasses four immunologically reactive peptides corresponding to regions of HTLV-2 proteins encoded by the env and gag genes. The invention further encompasses functionally equivalent variants thereof which do not significantly affect the antigenic properties of the peptides. For instance, conservative substitution of amino acid residues, one or a few amino acid deletions, or substitution of amino acid residues by amino acid analogues are within the scope of the invention. Homologs are peptides which have conservatively substituted amino acid residues. Amino acids which can be conservatively substituted for one another include but are not limited to: glycine, alanine; valine, isoleucine, leucine; asparagine, glutamine; aspartic acid, glutamic acid; serine, threonine; lysine, arginine; and phenylalanine, tyrosine. Homologous peptides are considered to be within the scope of the invention if they are recognized by antibodies which recognize the peptides designated H-HTLV-2, O-HTLV-2, T-HTLV-2 and Gag-1-HTLV-2 the sequences of which are shown below. All peptides corresponding to the peptides of the present invention but derived from different HTLV-2 isolates are also encompassed by the scope of this invention. Analogues are defined as peptides which are functionally equivalent to the present peptides but which contain certain non-naturally occurring or modified amino acid residues. Additionally, polymers of one or more of the peptides, and peptide analogues or homologs are within the scope of the invention. Also within the scope of this invention are peptides of fewer amino acid residues than H-HTLV-2, O-HTLV-2, T-HTLV-2 and Gag-1-HTLV-2 but which encompass one or more epitopes present in any one of the peptides.

The peptides were synthesized by known solid phase peptide synthesis techniques. Merrifield and Barany, The Peptides: Analysis, Synthesis, Biology, Vol. 1, Gross and Meinenhofer, eds., Academic Press, New York, Chap. 1 (1980). The synthesis also allows for one or more amino acids not corresponding to the original protein sequence to be added to the amino or carboxyl terminus of the peptide. Such extra amino acids are useful for coupling the peptides to another peptide, to a large carrier protein or to a solid support. Amino acids that are useful for these purposes include tyrosine, lysine, glutamic acid, aspartic acid, cysteine and derivatives thereof. Additional protein modification techniques may be used, e.g., $NH_2$-acetylation or COOH-terminal amidation, to provide additional means for coupling the peptides to another protein or peptide molecule or to a support. Procedures for coupling peptides to each other, carrier proteins and solid supports are well known in the art. Peptides containing the above-mentioned extra amino acid residues either carboxy or amino terminally, uncoupled or coupled to a carrier or solid support are consequently within the scope of the invention.

It has previously been found that synthetic peptides are useful in the detection of and immunization against HTLV-1. These findings are recorded in the PCT patent publication, W089-08664, published Sep. 21, 1989.

The novel peptide sequences are set forth below. The amino acid residues are derived from the nucleotide sequence previously described by Shimotohno (1985).

Peptide H-HTLV-2

X-Ile-Thr-Ser-Glu-Pro-Thr-Gln-Pro-Pro-Pro-Thr-Ser-Pro-Pro-Leu-Val-His-Asp-Ser-Asp-Leu-Glu-His-Val-Y-Z wherein X is either a hydrogen atom of the amino terminal $NH_2$ group of the peptide or an additional amino acid being selected to facilitate coupling of the peptide to a carrier; Y is absent or Cys; and Z is a hydroxy or amino group. The carboxy terminus of the peptide may be, but is not limited to, any of the following, an amino group, a hydroxy group, a Cys residue, a Cys residue followed by an amino group and a Cys residue followed by a hydroxy group. Peptide H-HTLV-2 in which X is either a hydrogen atom (H), Y is Cys and Z is a hydroxy group (OH) is particularly preferred.

Peptide O-HTLV-2

X-Ile-Lys-Pro-Asn-Arg-Gln-Gly-Leu-Gly-Tyr-Tyr-Ser-Pro-Ser-Tyr-Asn-Asp-Pro-Cys-Ser-Leu-Y-Z wherein X, Y, and Z have the same definitions as above. Peptide O-HTLV-2 in which X is H, Y is Cys and Z is OH is particularly preferred.

Peptide T-HTLV-2

X-Pro-Leu-Val-His-Asp-Ser-Asp-Leu-Glu-His-Val-Leu-Thr-Pro-Ser-Thr-Ser-Trp-Thr-Thr-Lys-Ile-Leu-Lys-Y-Z wherein X, Y, and Z have the same definitions as above. Peptide T in which X is H, Y is Cys-and Z is OH is particularly preferred.

Peptide GAG-1-HTLV-2

X-Ser-Pro-Glu-Ala-His-Val-Pro-Pro-Pro-Tyr-Val-Glu-Pro-Thr-Thr-Thr-Gln-Cys-Phe-Y-Z wherein X, Y, and Z have the same definitions as above. Peptide GAG-1-HTLV-2 in which X is H, Y is Cys and Z is OH is particularly preferred.

The peptides are useful for diagnosing HTLV-2 infection, for distinguishing between HTLV-1 and HTLV-2 infection and in screening blood and blood-derived products with a high degree of reliability and specificity. The peptides are also useful as vaccines to protect against future infection by HTLV-2. The invention also provides monoclonal and polyclonal antibodies which specifically recognize the peptides.

The peptides can be used in methods of detecting antibodies to HTLV-2 in biological samples including but not limited to sera, other body fluids, tissue samples and samples which may contain antibodies to HTLV-2. The screening methods are rapid, efficient and allow for simultaneous screening of numerous samples. The methods involve contacting the sample with the peptides under conditions which allow an immunological complex to form between the peptide and any HTLV-2 specific antibodies which may be present in the sample. Measuring of complex formation, if any, by suitable detection means determines the presence or absence of antibodies to HTLV-2 in the sample.

Such detection methods include out are not limited to homogeneous and heterogeneous binding immunoassays, such as radioimmunoassays (RIA), ELISA and Western blot analyses. Further, the assay protocols using the novel peptides allow for competitive and noncompetitive binding studies to be performed.

The peptides may be labeled (signal-generating) or unlabeled depending on the type of assay used. Labels which may be coupled to the peptides are those known in the art and include but are not limited to enzymes, radionuclides, fluorogenic and chromogenic substrates, cofactors, biotin/ avidin, colloidal gold, and magnetic particles.

The peptides can be coupled by any means known in the art to other peptides, solid supports and carrier proteins. Solid supports include but are not limited to polystyrene or polyvinyl microtiter plates, glass tubes or glass beads and chromatographic supports, such as paper, cellulose and cellulose derivatives, and silica. Carrier proteins include but are not limited to bovine serum albumin (BSA) and keyhole limpet hemacyanin (KLH).

Preferred assay techniques, especially for large scale clinical screening of patient sera and blood and blood-derived products are ELISA, agglutination and Western blot, ELISA tests being particularly preferred for speed, the ability to assay numerous samples simultaneously and ease of automation. ELISA tests employing the peptides described above are based on those currently in use for detection of other human viruses. For use as reagents in these assays, the peptides are conveniently bonded to the inside surface of microtiter wells. The peptides may be directly bonded by hydrophobic interactions to the microtiter well, or attached covalently by means known in the art to a carrier protein, such as BSA, with the resulting conjugate being used to coat the wells, again by hydrophobic interactions. The peptides are generally used in a concentration of approximately 1-100 μM although this range is not limiting. Generally the peptides are used in a concentration of between 10 to 100 μg/ml for coating.

Samples including but not limited to body fluids and tissue samples, are then added to the peptide coated wells where an immunological complex forms if antibodies to HTLV-2 are present in the sample. A signal generating means may be added to aid detection of complex formation. A detectable signal is produced if HTLV-2 specific antibodies are present in the sample. Agglutination assays are commonly used in Japan. Either latex or erythrocytes can be used in the technique. The methods used in agglutination assays are well in the art of blood screens.

The peptides of the invention may also be formulated into compositions for use as immunogens. These immunogens can be used as vaccines or to elicit production of polyclonal and monoclonal antibodies in animals. For formulation of such compositions, an immunogenically effective amount of at least one of the peptides is admixed with a physiologically acceptable carrier suitable for administration to animals and man. The peptides may be covalently attached to each other, to other peptides, to a protein carrier or to other carriers, incorporated into liposomes or other such vesicles, and/or mixed with an adjuvant or adsorbent as is known in the vaccine art. Alternatively, the peptides are uncoupled and merely admixed with a physiologically acceptable carrier such as normal saline or a buffering compound suitable for administration to animals and man.

As with all immunogenic compositions for eliciting antibodies, the immunogenically effective amounts of the peptides of the invention must be determined empirically. Factors to be considered include the immunogenicity of the native peptide, whether or not the peptide will be complexed with or covalently attached to an adjuvant or carrier protein or other carrier and route of administration for the composition, i.e. intravenous, intramuscular, subcutaneous, etc., and the number of immunizing doses to be administered. Such factors are known in the vaccine art and it is well within the skill of immunologists to make such determinations without undue experimentation.

The invention is further illustrated by the following specific examples which are not intended in any way to limit the scope of the invention.

EXAMPLE 1

Peptide Synthesis

An Applied Biosystems peptide-synthesizer Model 430 A, was utilized for peptide synthesis. The peptides were synthesized according to the Users Manual for Peptide Synthesizer Model 430A, Applied Biosystems, (1986). Each synthesis used a p-methylbenzylhydrylamine solid phase support resin (Peptides International, Louisville, Ky.). All amino acids for use in synthesis contained t-butylcarbonyl groups (t-Boc) protecting the $-NH_2$ group and were obtained from Novabiochem AG, Switzerland. Amino acids with reactive side chain groups contained additional protective groups to prevent unwanted and undesirable side chain reacrions. The individual amino acid residues used in synthesizing all of the peptides are set forth in Table 1.

TABLE 1

| Amino Acids Used in the Synthesis of Peptides |
|---|
| Boc—Ala—OH |
| Boc—Arg (Tos)—OH |
| Boc—Asn—OH |
| Boc—Asp (OBzl)—OH |
| Boc—Cys (pMeOBzl)—Oh |
| Boc—Glu (OBzl)—OH |
| Boc—Gln—OH |
| Boc—Gly—OH |
| Boc—His—(Tos)—OH |
| Boc—Ile—OH ½ $H_2O$ |
| Boc—Leu—OH $H_2O$ |
| Boc—Lys (2-Cl—Z)—OH (cryst.) |
| Boc—Met—OH |
| Boc—Phe—OH |
| Boc—Pro—OH |
| Boc—Ser (Bzl)—OH DCHA |
| Boc—Thr (Bzl)—OH |
| Boc—Trp (Formyl)—OH |
| Boc—Tyr (2-Br—Z)—OH |
| Boc—Val—OH |

Tos: Tosyl or p-Toluene sulfonic acid
oBzl = Benzyloxy
pMeoBzl = p-Methylbenzyloxy
2-CL—Z = Carbobenzoxy chloride
2-Br—Z = Carbobenzoxy bromide After completion of synthesis, the protecting groups were removed from the synthesized peptide and the peptide was cleaved from the solid support resin by treatment at 0° C. with anhydrous hydrofluoric acid (HF) combining 10% anisole and 10% dimethylsulfide as scavenging agents. After cleavage, the HF in the sample was purged under a stream of $N_2$, with removal of any residual HF accomplished by subjecting the sample to vacuum at 0° C. The peptides were extracted from the resin by treatment with trifluoroacetic acid (TFA) which was then removed by evaporation at room temperature. Following TFA removal, the peptides were precipitated and washed with anhydrous ether.

Prior to use in specific assays, the peptides are further purified, if desired, by reverse phase high performance liquid chromatography (HPLC). A particularly suitable column for such purification is the reverse-phase Vydek C-18 column using a water trifluoroacetate (TFA)-acetonitrile (TFA) gradient to elute the peptides.

EXAMPLE 2

Preparation of Microtiter Plates for ELISA Assay

To facilitate coating of the wells of the microtiter plates, the peptides are conjugated to Bovine Serum Albumin (BSA).

For production of 200 peptide coated microtiter plates the following protocol is used.

An aliquot of 0.15 g BSA (Boerhinger Mannheim, fraction V) is dissolved in 3 ml coupling buffer (0.2M Na $PO_4$, pH 8.5). This BSA solution is divided into three equal volumes each of which is applied to PD-10 column (Pharmacia AB, Uppsala Sweden) followed by 1.5 ml coupling buffer and eluted with 2.0 ml coupling buffer. The BSA concentration of the pooled eluate samples is calculated by measuring the absorbance of the solution at 280nm, where A (0.1% BSA) =0.67 ml/mg. The recovery is generally 80-90%.

N-succinimidyl 3-(2-pyridyldithio) propionate (SPDP, Pharmacia) is then dissolved in ethanol to a final concentration of 5-40mM. The concentration of SPDP is determined by measuring the reactive ester according to the Pharmacia Fine Chemicals SPDP brochure. 2-pyridyldisulfide residues are introduced into the BSA prepared as above by adding ten SPDP equivalents to each BSA equivalent. The SPDP solution is introduced to the BSA solution with stirring. The mixture is then incubated for 15-30 minutes at room temperature.

To remove excess unreacted SPDP, the pyridyldisulfide-BSA mixture is aliquoted into 6 equal volumes each of which is applied to a PD-10 column. The columns are equilibrated and the product is eluted with 10% acetic acid in water. The degree of substitution is measured according to the Pharmacia Fine Chemicals SPDP brochure. The recovery of BSA is generally 90-120 mg and the degree of substitution is approximately 7 with a range of 6-8.

The peptide solution is made by mixing 25 mg peptide and an amount of the pyridyldisulfide-BSA solution to make seven peptide equivalents to one BSA equivalent. The mixture is incubated for 18-48 hours at room temperature. The released 2-thiopyridone is removed by running the reaction mixture over a column (2.0cm$^2$, 80-100 ml) packed with Sephadex G-25 (Pharmacia-LKB), equilibrated with 10% acetic acid in water. The product is eluted with 10% acetic acid in water. The fractions with $A_{280}$ greater than 0.5 are then collected and pooled. The pooled volume is approximately 30-40 ml. The $A_{280}$ of the pooled fractions is measured and the BSA concentration is calculated. The pooled fractions are stored at 4° C. and are stable for months.

The peptide-BSA conjugate is then diluted in coating buffer (50mM $NaCo_3$, 0.15M Nacl, pH 9.5) to 60 mg/ml. The pH of the solution is checked and adjusted with 1-5M NaOH, to 9.5.

An aliquot of 100 μl of the peptide-BSA mixture in coating buffer is placed in each well of a microtiter plate (Nunc, High Binding, catalog No. 4-68667). The plates are incubated for 15 minutes at room temperature. After the incubation, the liquid is aspirated from the wells. An aliquot of 200 μl sterile, (0.22 μm-filtered) 3% BSA in phosphate buffered saline (PBS, 10mM $NaPO_4$, 0.15M Nacl, pH 7.2) is added to each well. The plates are covered and incubated for sixteen hours at 37° C.

After the incubation, the liquid is aspirated from the wells. The microtiter plates are placed in a safety cabinet and air dried for about three hours.

The plates can be stored for a long time at +4° C. or −20° C. in any closed container, for instance in sealed aluminum bags. The presence of a drying agent such as silica gel aids in preservation of the plates.

EXAMPLE 3

ELISA Methods

The peptides were used in an ELISA test to measure their immunologic reactivity. All peptides were run in parallel ELISA tests against serum samples positive for antibodies to HTLV-2, serum samples positive for antibodies to HTLV-1 and 10 blood donor sera negative for HTLV-1/HTLV-2. The sera were also tested against HTLV-1 peptides which have been previously described in PCT patent publication, WO89-08664, published Sep. 21, 1989.

The microtiter plates are prepared as in Example 2. If the plates have been stored they may first be brought to room temperature and then they may be pre-soaked for ten minutes in wash buffer (0.05% Tween 20 in PBS). The presoak solution is then aspirated from the wells prior to use.

The serum samples are each diluted 1:50 in serum dilution solution (1% BSA in wash buffer). An aliquot of 100 μl diluted serum is placed in each well and the plates are incubated for 90 minutes at 37° C. in a humidifier. After the incubation, the plates are washed three times with wash buffer.

Anti-human immunoglobulin G (IgG) conjugate (Jacksson, from Labassco, art. nr. 10.4999999, 109-056-003, Alkaline Phosphatase) is dissolved in 0.5 ml $H_2O$, aliquoted serum dilution buffer. An aliquot of 100 μl is added to each well. The plates are incubated for 90 minutes at 37° C. in a humidified chamber. After the incubation, the plates are washed three times with wash buffer.

Alkaline phosphatase substrate (Sigma, tablets) is dissolved in substrate dilution buffer (50mM $Na_2CO_3$, 1mM $MgCl_2$) to a final concentration of 1 mg/ml. An aliquot of 200 μl is added to each well. The plates are incubated for approximately 35 minutes at room temperature. If desired the reaction can be stopped by the addition of 100 μl 3M NaOH per well.

To determine the amount of antibody bound to the peptides in each well, the plates are read at 405 nm. The higher the absorbance, the greater the amount of bound antibody.

EXAMPLE 4

ELISA Test of Initial Peptides with HTLV-2 and HTLV-1 Positive Sera

Peptides of the present invention were selected from an initial group of peptides which shared homology with putative HTLV-1 epitopes. The amino acid sequences of the initial group of peptides are shown in Table 2. The amino acid sequences were derived from the nucleotide sequence described by Shimitohno (1985) This initial group of peptides was tested with patient sera by the method described in Example 3 to determine the ability of the particular peptides to detect antibodies which recognize HTLV-2 and to determine the cross-reactivity of the peptides to antibodies which recognize HTLV-1.

The serum samples used in this screening test were confirmed HTLV-2 positive by PCR analysis. The sera designated HT-201-HT-220 were obtained from Serologicals Inc., Pensacola, Fla. Previous researchers were unable to distinguish between antibodies specific for either HTLV-1 or HTLV-2 in these sera by any of Western blot analyses, ELISA tests and immunofluorescence assays.

218 and HT-219. These sera were found to be only weakly positive with previous ELISA tests indicating that the level of HTLV-2 specific antibodies in these sera was low. Surprisingly, the peptides of the present invention react well with HTLV-2 infected patient sera and react poorly with antibodies present in HTLV-1 infected patient sera. The Gag-1-HTLV-2 peptide is not as specific as the other three peptides, therefore H-

TABLE 2

Amino Acid Sequences of Initial Group of Peptides
(excluding H-HTLV-2, T-HTLV-2, O-HTLV-2 and Gag-1-HTLV-2)

AA-HTLV-2
Ser—Leu—Leu—Leu—Glu—Val—Asp—Lys—Asp—Ile—Ser—His—Leu—Thr—Gln—Ala—Ile—Val—Lys—Asn—His—Gln—Asn
A-HTLV-2
Gly—Leu—Asp—Leu—Leu—Phe—Trp—Glu—Gln—Gly—Gly—Leu—Cys—Lys—Ala—Ile—Gln—Glu—Gln—Cys—Cys—Phe—Leu—Asn
B-HTLV-2
Trp—Thr—His—Cys—Tyr—Gln—Pro—Arg—Leu—Gln—Ala—Ile—Thr—Thr—Asp—Asn—Cys—Asn—Asn—Ser—Ile—Ile—Leu
C-HTLV-2
Tyr—Ser—Cys—Met—Val—Cys—Val—Asp—Arg—Ser—Ser—Leu—Ser—Ser—Trp—His—Val—Leu—Tyr—Thr—Pro
HH-HTLV-2
Leu—Val—His—Asp—Ser—Asp—Leu—Glu—His—Val—Leu—Thr—Pro—Ser—Thr—Ser—Trp—Thr—Thr—Lys—Ile
V-HTLV-2
Val—Leu—Tyr—Thr—Pro—Asn—Ile—Ser—Ile—Pro—Gln—Gln—Thr—Ser—Ser—Arg—Thr—Ile—Leu—Phe—Pro—Ser—Leu—Ala
X-HTLV-2
Asn—Ser—Ile—Ile—Leu—Pro—Pro—Phe—Ser—Leu—Ala—Pro—Val—Pro—Pro—PropAla—Thr—Arg—Arg—Arg—Arg Table 3 shows the results obtained by the ELISA test. The negative controls are sera negative for both HTLV-1 and HTLV-2 and are designated NC-1 and NC-2, the HTLV-1 positive serum is designated HTLV-1. The patient sera HT-201-HT-220 are designated 201-220. The results presented are absorbance readings at 405nm.

HTLV-2, T-HTLV-2 and O-HTLV-2 are the preferred peptides of the present invention.

It is surprising that the remaining peptides were unable to detect antibodies to HTLV-2 in the majority of patient sera. These peptides correspond to purported HTLV-1 epitopes and were therefore expected to react well with HTLV-2 antibodies.

TABLE 3

ELISA Analysis of HTLV-2 Peptides Using Defined HTLV-2 or HTLV-1 Serum Samples.

| Serum Sample | A | AA | B | C | Gag 1 | H | HH | O | T | V | X |
|---|---|---|---|---|---|---|---|---|---|---|---|
| NC-1 | 0.134 | 0.111 | 0.115 | 0.107 | 0.152 | 0.095 | 0.121 | 0.130 | 0.129 | 0.159 | 0.122 |
| NC-20 | 0.119 | 0.087 | 0.106 | 0.114 | 0.108 | 0.091 | 0.106 | 0.110 | 0.115 | 0.107 | 0.094 |
| HTLV-1 | 1.759 | 0.126 | 0.146 | 0.180 | 2.809 | 0.149 | 0.201 | 0.170 | 0.136 | 0.163 | 0.159 |
| 201 | 0.102 | 0.079 | 0.090 | 0.105 | 0.905 | 3.482 | 0.101 | 1.340 | 1.080 | 0.110 | 0.102 |
| 202 | 0.118 | 0.088 | 0.100 | 0.095 | 0.458 | 1.423 | 0.107 | 1.434 | 0.706 | 0.122 | 0.113 |
| 203 | 0.111 | 0.095 | 0.100 | 0.088 | 0.370 | 0.662 | 0.105 | 0.108 | 0.455 | 0.102 | 0.145 |
| 204 | 0.226 | 0.092 | 0.092 | 0.092 | 0.537 | 0.985 | 0.118 | 0.097 | 0.713 | 0.092 | 0.103 |
| 205 | 0.308 | 0.093 | 0.100 | 0.109 | 1.587 | 3.649 | 2.074 | 1.501 | 3.402 | 0.123 | 0.103 |
| 206 | 0.137 | 0.096 | 0.125 | 0.113 | 0.591 | 3.010 | 0.130 | 0.517 | 2.248 | 0.119 | 0.132 |
| 207 | 0.105 | 0.092 | 0.122 | 0.098 | 0.180 | 0.255 | 0.116 | 0.168 | 0.213 | 0.112 | 0.147 |
| 208 | 0.120 | 0.085 | 0.097 | 0.090 | 0.390 | 1.426 | 0.110 | 0.106 | 1.153 | 0.106 | 0.105 |
| 209 | 0.121 | 0.083 | 0.091 | 0.084 | 0.480 | 3.587 | 0.104 | 0.424 | 1.741 | 0.113 | 0.097 |
| 210 | 0.104 | 0.088 | 0.103 | 0.126 | 0.270 | 0.604 | 0.120 | 0.099 | 0.375 | 0.095 | 0.148 |
| 211 | 1.823 | 0.083 | 0.095 | 0.094 | 2.010 | 3.864 | 0.113 | 3.660 | 3.173 | 0.122 | 0.091 |
| 212 | 0.113 | 0.087 | 0.097 | 0.088 | 1.283 | 1.901 | 0.103 | 1.068 | 1.365 | 0.099 | 0.100 |
| 213 | 0.154 | 0.102 | 0.101 | 0.121 | 0.156 | 0.736 | 1.625 | 0.104 | 0.529 | 0.105 | 0.104 |
| 214 | 0.105 | 0.094 | 0.106 | 0.523 | 0.234 | 2.510 | 0.158 | 3.525 | 1.385 | 0.099 | 0.109 |
| 215 | 0.234 | 0.124 | 0.195 | 0.435 | 2.287 | 3.787 | 0.372 | 3.526 | 3.292 | 0.172 | 0.232 |
| 216 | 0.117 | 0.082 | 0.091 | 0.095 | 0.474 | 1.017 | 0.099 | 1.126 | 1.004 | 0.102 | 0.099 |
| 217 | 0.118 | 0.080 | 0.088 | 0.082 | 0.132 | 1.429 | 0.099 | 0.444 | 1.395 | 0.101 | 0.092 |
| 218 | 0.094 | 0.079 | 0.079 | 0.076 | 0.121 | 0.142 | 0.086 | 0.090 | 0.134 | 0.090 | 0.084 |
| 219 | 0.104 | 0.084 | 0.092 | 0.087 | 0.115 | 0.117 | 0.108 | 0.108 | 0.106 | 0.102 | 0.101 |
| 220 | 0.162 | 0.096 | 0.134 | 0.101 | 0.477 | 1.342 | 0.113 | 0.048 | 1.045 | 0.118 | 0.137 |

The results presented in Table 3 clearly show that out of the series of initial peptides only those claimed in the present application (H-HTLV-2, O-HTLV-2, T-HTLV-2 and Gag-1-HTLV-2) react strongly with antibodies present in HTLV-2 infected patient sera. All of the peptides react poorly with the sera designated HT- The specificity of the H-HTLV-2, T-HTLV-2 and O-HTLV-2 peptides is surprising and of particular benefit in blood screening and patient diagnosis.

EXAMPLE 5

Specificity of the Peptides

In order to better define the specificity of the peptides, ELISA tests were done as described in Example 3. The peptides of the present invention and peptides derived from corresponding regions of HTLV-1 were tested against both HTLV-1 and HTLV-2 positive sera. The patient sera were obtained from Dr. William Hall, Cornell University, N.Y.

Table 4 shows the results obtained. The sera designated 2a, 2b, 2c, 2d, 2e and 2f were obtained from five different patients and were HTLV-2 positive as determined by polymerase chain reaction (PCR) analysis and were also human immunodeficiency virus (HIV) positive. The sera designated 1a, 1b1c, 1d, 1e and 1f were obtained from five different patients and were HTLV-1 positive as determined by PCR analysis. Patients 1a, 1b and 1c have adult T cell leukemia and patients 1d, 1 e and 1f are HIV positive. Sera designated HIV-1 were obtained from patients who are neither HTLV-1 nor HTLV-2 positive but are HIV positive. Sera designated NL-1 and NL-2 are negative controls obtained from patients not infected with either HTLV-1 or HTLV-2.

The numbers shown in Table 4 are the average of two experiments and are the absorbance readings at 405nm.

TABLE 4

ELISA Results of Peptides Derived From HTLV-1 and HTLV-2 From Corresponding Regions

| Patient | H-HTLV-1 | H-HTLV-2 | T-HTLV-1 | T-HTLV-2 | O-HTLV-1 | O-HTLV-2 |
|---------|----------|----------|----------|----------|----------|----------|
| 2a | 0.016 | 1.162 | 0.026 | 0.908 | 0.055 | 1.753 |
| 2a | 0.041 | 1.441 | 0.068 | 1.228 | 0.043 | 1.000 |
| 2a | 0.051 | 1.803 | 0.078 | 1.476 | 0.040 | 0.846 |
| 2d | 0.028 | 0.925 | 0.054 | 0.774 | 0.049 | 1.338 |
| 2e | 0.039 | 1.371 | 0.043 | 1.729 | 0.069 | 0.648 |
| 2f | 0.023 | 1.788 | 0.048 | 1.644 | 0.060 | 0.757 |
| 1a | 1.889 | 0.044 | 1.735 | 0.072 | 1.742 | 0.072 |
| 1b | 1.963 | 0.091 | 1.773 | 0.100 | 1.963 | 0.076 |
| 1c | 1.865 | 0.027 | 1.838 | 0.130 | 1.878 | 0.096 |
| 1d | 1.938 | 0.062 | 1.830 | 0.109 | 1.508 | 0.098 |
| 1e | 1.923 | 0.065 | 1.799 | 0.043 | 1.466 | 0.124 |
| 1f | 1.872 | 0.044 | 1.912 | 0.076 | 1.757 | 0.088 |
| HIV-1 | 0.079 | 0.089 | 0.053 | 0.130 | 0.100 | 0.127 |
| HIV-1 | 0.061 | 0.052 | 0.096 | 0.110 | 0.110 | 0.112 |
| NL-1 | 0.033 | 0.101 | 0.098 | 0.105 | 0.123 | 0.132 |
| NL-2 | 0.028 | 0.078 | 0.092 | 0.107 | 0.116 | 0.126 |
| NO serum | 0.020 | 0.082 | 0.052 | 0.095 | 0.049 | 0.083 |

The results obtained illustrate the high degree of specificity obtained by the peptides of the present invention.

It is evident from the foregoing results that the novel synthetic peptides, described herein, which correspond to regions of proteins encoded by the env and gag genes of HTLV-2, clearly provide unique reagents for sensitive assays for the presence of antibodies to HTLV-2. Also, peptides H-HTLV-2 clearly discriminate between antibodies which recognize HTLV-1 and antibodies which recognize HTLV-2.

We claim:

1. A peptide of the sequence:
   Ile-Thr-Ser-Glu-Pro-Thr-Gln-Pro-Pro-Pro-Thr-Ser-Pro-Pro-Leu-Val-His-Asp-Ser-Asp-Leu-Glu-His-Val-Y wherein Y is either absent or a cysteine residue.

2. A peptide according to claim 1, wherein Y is absent.

* * * * *